United States Patent
Pigott

(10) Patent No.: US 6,591,144 B2
(45) Date of Patent: Jul. 8, 2003

(54) STEERABLE CATHETER AND METHOD FOR LOCATING CORONARY SINUS

(75) Inventor: John D. Pigott, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 10/044,587

(22) Filed: Oct. 23, 2001

(65) Prior Publication Data

US 2003/0078645 A1 Apr. 24, 2003

(51) Int. Cl.[7] .................................................. A61N 1/00
(52) U.S. Cl. ......................................... 607/119; 600/323
(58) Field of Search ................................ 607/119–132; 600/322–340, 372–377

(56) References Cited

U.S. PATENT DOCUMENTS

| | | | |
|---|---|---|---|
| 3,847,483 A | 11/1974 | Shaw et al. .................... 356/41 |
| 4,697,593 A | 10/1987 | Evans et al. ................. 128/634 |
| 4,796,636 A | 1/1989 | Branstetter et al. ......... 128/633 |
| 5,168,864 A | 12/1992 | Shockey ........................ 128/4 |
| 5,265,601 A | 11/1993 | Mehra ............................ 607/9 |
| 5,277,181 A | 1/1994 | Mendelson et al. ......... 128/633 |
| 5,531,686 A | 7/1996 | Lundquist et al. ............ 604/95 |
| 5,597,377 A | 1/1997 | Aldea .......................... 600/16 |
| 5,891,088 A | 4/1999 | Thompson et al. ............ 604/95 |
| 5,902,324 A | 5/1999 | Thompson et al. ............ 607/9 |
| 5,906,590 A | 5/1999 | Hunjan et al. ................. 604/95 |
| 6,031,603 A | 2/2000 | Fine et al. ..................... 356/41 |
| 6,033,378 A | 3/2000 | Lundquist et al. ............. 604/95 |
| 6,070,100 A | 5/2000 | Bakels et al. ................... 607/9 |
| 6,122,545 A | 9/2000 | Struble et al. .................. 607/9 |
| 6,122,552 A * | 9/2000 | Tockman et al. ............ 607/116 |
| 6,178,356 B1 | 1/2001 | Chastain et al. ............ 607/128 |
| 6,223,079 B1 | 4/2001 | Bakels et al. ................... 607/9 |
| 6,264,627 B1 * | 7/2001 | Liska et al. .................... 604/29 |
| 6,266,563 B1 | 7/2001 | KenKnight et al. ............ 607/5 |
| 6,363,288 B1 * | 3/2002 | Bush et al. ................. 607/122 |

* cited by examiner

*Primary Examiner*—George R. Evanisko
*Assistant Examiner*—Omar Khan
(74) *Attorney, Agent, or Firm*—Olson & Hierl, Ltd.

(57) ABSTRACT

A steerable catheter includes an elongate cannula having a proximal end and a distal end. A blood characteristic sensor, such as an oxygen sensor, is connected to the cannula and disposed to sense percent oxygen saturation of blood at the distal end of the cannula. The blood oxygen sensor generates a signal indicative of percent oxygen saturation. An oximetry display is responsive to the signal and capable of displaying sensed percent oxygen saturation in a form understandable by an operator. A steering mechanism is operably connected to the cannula and is selectively operable by an operator to deflect the distal end of the cannula. A method of locating the coronary sinus of a heart involves endovascularly introducing a catheter into the right atrium, sensing percent oxygen saturation at the distal end of the catheter, and steering the catheter toward a region of lowest percent oxygen saturation.

30 Claims, 7 Drawing Sheets

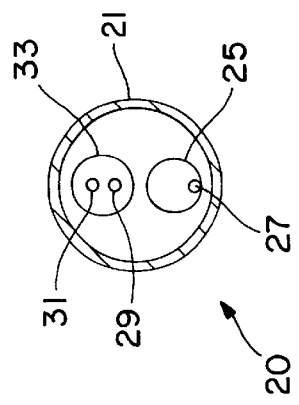
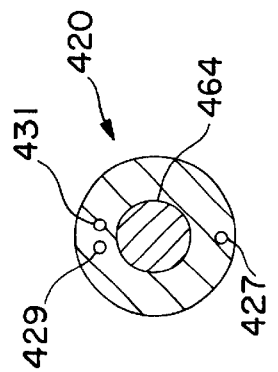
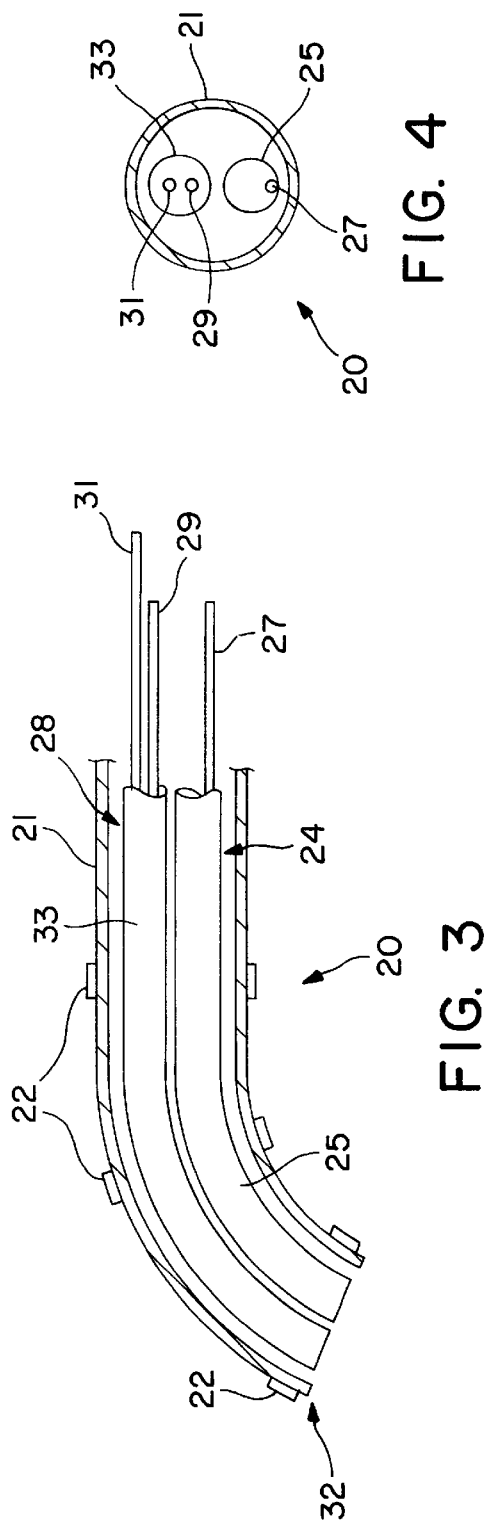
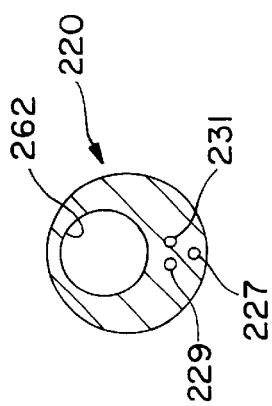
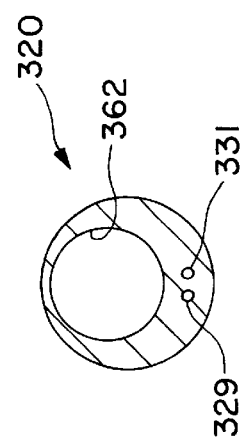

STEERABLE CATHETER AND METHOD FOR LOCATING CORONARY SINUS

TECHNICAL FIELD OF THE INVENTION

This invention relates generally to medical devices and methods for locating the coronary sinus of a heart and preferably placing an electrical lead for use with an implantable pulse generator.

BACKGROUND OF THE INVENTION

Many cardiac disorders, such as bradycardia, tachycardia and ventricular fibrillation, for example, involve abnormalities of cardiac rhythm or rate. Implantable electrical pulse generators are commonly used to treat such disorders. Modern implantable pulse generators include an hermetically sealed housing containing control electronics and a battery, and have standard connectors to which implantable electrical leads can be connected. Such leads include insulated conductors and one or more exposed electrodes near the distal end of the lead for electrically connecting the pulse generator to one or more chambers of the heart. Sensing electrodes sense the electrical activity of the heart so that electrical markers of the electrocardiogram such as the P-wave or R-wave can be detected. Stimulating electrodes conduct pulses of electrical energy from the pulse generator to excitable cardiac tissue. Often both types of electrodes are employed, with the nature and timing of the stimulation pulses being related to the sensed electrical activity. Selected placement of the leads and electrodes permits delivery of therapeutic electrical pulses appropriate to the disorder to be treated.

Lead systems for use with modern implantable pulse generators can include single lead systems and multiple lead systems, with single or dual chamber sensing or therapy. Some systems provide four-chamber sensing and therapy. Examples of such systems can be found in Dual Chamber Cardiac Pacing from a Single Electrode, U.S. Pat. No. 5,265,601; Bi-atrial and/or Bi-ventricular Sequential Cardiac Pacing Systems, U.S. Pat. No. 5,902,324; Bi-ventricular Pacing Method, U.S. Pat. No. 6,223,079; and Multiple Channel Sequential Cardiac Pacing Method, U.S. Pat. No. 6,122,545, all incorporated by reference.

Although leads and electrodes can be applied directly to the epicardium via thoracotomy, it is generally preferred to insert the leads endovascularly into a chamber of the heart, when possible. In most single lead systems, the lead is passed through the superior vena cava, right atrium and tricuspid valve, and into the right ventricle. The electrode is fixed within the right ventricle usually at the apex position. In many multiple lead systems and some single lead systems, one lead is passed through the superior vena cava, right atrium and coronary sinus, generally with the aid of fluoroscopy, and fixed within the great vein or a deep coronary vein to locate the electrode in proximity to the left atrium or left ventricle.

Determining the location of the coronary sinus and placing a lead therein can be difficult. The lead must traverse an angle to enter the orifice of the coronary sinus in the wall of the right atrium. The difficulty of locating the coronary sinus and placing a lead therein is especially great in patients with congestive heart failure and dilated cardiomyopathy. In such patients, the heart is enlarged and the location of the coronary sinus can vary significantly from the location in a heart with normal anatomy. Nevertheless, the ongoing need to place endovascular cardiac leads in patients with an unusually disposed coronary sinus is expected to increase. This is because of the emerging use of implantable pulse generators to treat congestive heart failure.

Implantable pulse generators may be particularly useful for treating congestive heart failure ("CHF") manifested by conduction defects or other cardiomyopathies. In a healthy person, the electrical conduction system of the heart sends signals to the chambers of the heart that cause them to contract in a precise pattern to pump blood throughout the circulatory system. In people with congestive heart failure, however, the electrical conduction system is often impaired and fails to coordinate the contractions of the heart's chambers. In many patients with CHF, the left and right ventricles no longer contract in the usual synchronized manner. This can reduce cardiac output, leading to symptoms such as shortness of breath, fatigue, and swelling of the feet and ankles.

A promising therapy for treating congestive heart failure through the use of implantable pulse generators is bi-ventricular pacing, also known as cardiac re-synchronization. By sensing and pacing the left and right ventricles separately, the desired timing of the contractions of the ventricles can be obtained. This will result in an increase in cardiac output.

Bi-ventricular pacing involves placement of right and left ventricular pacing leads. The procedure for placing a pacing lead within a right ventricle is well known and has been effectively practiced for decades. In contrast, it is not desirable to place a pacing lead within the left ventricle. A lead passing through the left atrium and mitral valve into the left ventricle could interfere with complete closure of the valve, thereby impairing the performance of the left ventricle in pumping oxygenated blood throughout the body. Also, pacing leads may be a site of clot formation. Such clots, if dislodged, may cause serious problems in-the arterial circulation system, e.g., stroke. Pacing of the left ventricle can be achieved by placing a lead into a branch of the coronary sinus that overlies the left ventricle. As noted above, placing a left ventricular pacing lead into the coronary sinus can be extremely difficult even when performed by the most experienced electrophysiologists.

Preformed catheters have been used to permit access to the coronary sinus via the superior vena cava and right atrium. The use of such preformed catheters is complicated in patients with CHF and dilated cardiomyopathy because the location of the coronary sinus is quite variable. In recent clinical trials of bi-ventricular pacing, cannulation of the coronary sinus was attempted by experienced and expert electrophysiologists who cannulate the coronary sinus daily for arrhythmia testing. Despite their experience and expertise, the coronary sinus was successfully accessed only 85 percent of the time.

If bi-ventricular pacing is to become a widely used treatment for congestive heart failure, then reliable and easy access to the coronary sinus must be provided. There are insufficient numbers of experienced electrophysiologists to accommodate the demand for this therapy. The present invention permits cardiologists and others without daily experience accessing the coronary sinus to do so reliably. Other medical procedures that require endovascular access to the coronary sinus likewise will be facilitated by the present invention. An example of such a procedure is electrophysiologic testing when the coronary sinus is difficult to locate or cannulate.

SUMMARY OF THE INVENTION

The present invention relates to the medical procedure of accessing the orifice of the coronary sinus for the purpose of placing a medical device adjacent to or through the orifice. One such medical device is a permanent left ventricular pacing lead. Other medical devices include temporary sensing or pacing catheters for electrophysiologic testing.

According to one aspect, the present invention involves locating the orifice of the coronary sinus by sensing characteristics of blood emerging from the coronary sinus into the right atrium. One characteristic that is especially correlated with blood from the coronary sinus is oxygen content. The percent oxygen saturation in the coronary sinus is among the lowest in the human body. Other characteristics correlated with blood from the coronary sinus are lower pH and higher $CO_2$ concentration. By sensing the oxygen concentration, pH, $CO_2$ or other characteristic at the distal end of a medical device placed within the right atrium, and by steering the distal end of the medical device toward a region of lower oxygen concentration, lower pH or higher $CO_2$ concentration, for example, the location of the orifice of the coronary sinus can be determined. Once the orifice of the coronary sinus is located, the medical device can be introduced into the coronary sinus or used to establish a pathway for guiding another device into the coronary sinus. One such medical device is a left ventricular pacing lead.

The present invention also permits determination of oxygen saturations in other vascular structures. This may be particularly important in patients with congenital heart disease as well as in patients in whom specific organ venous and arterial oxygen saturations are needed to guide medical therapy.

According to another aspect of the invention, a steerable oximetric catheter includes an elongate cannula having a proximal end and a distal end. A blood oxygen sensor is connected to the cannula and is disposed to sense percent oxygen saturation of blood at the distal end of the cannula. The blood oxygen sensor generates a signal indicative of percent oxygen saturation. An oximetry display is responsive to the signal and is capable of displaying sensed percent oxygen saturation in a form understandable by an operator. A steering mechanism is operably connected to the cannula and selectively operable by an operator to deflect the distal end of the cannula toward a region of relatively low percent oxygen saturation.

Once the coronary sinus is located, a pacing lead can be inserted through the cannula to be fixed proximate to the coronary sinus or inserted into and fixed into the great vein or a coronary vein extending from the coronary sinus. The steerable catheter then can be removed. Alternatively, once the coronary sinus is located, a hollow sheath can be advanced over the steerable catheter and held at the coronary sinus. The steerable catheter then can be removed and the pacing lead can be inserted through the hollow sheath to have its distal end fixed in the coronary sinus or a coronary vein extending from it. The hollow sheath then can be removed.

The present invention also includes a kit comprising a steerable oximetric catheter and a sheath used to locate the pacing lead.

Further aspects and advantages of the present invention are apparent from the following description of preferred embodiments and methods, made with reference to the drawings.

BRIEF DESCRIPTION OF THE DRAWINGS

In the drawings,

FIG. 3 is an enlarged view of a portion of the embodiment of FIG. 2, shown cut-away;

FIG. 4 is an enlarged cross-sectional view of the embodiment of FIG. 2;

FIG. 8 is a cross-sectional view of the catheter of FIGS. 5 and 6;

FIG. 9 is a cross-sectional view of an alternative embodiment of a steerable, oximetric catheter;

FIG. 10 is a cross-sectional view of yet another alternative embodiment of a steerable, oximetric catheter.

DESCRIPTION OF THE PREFERRED EMBODIMENTS

Figure 1:
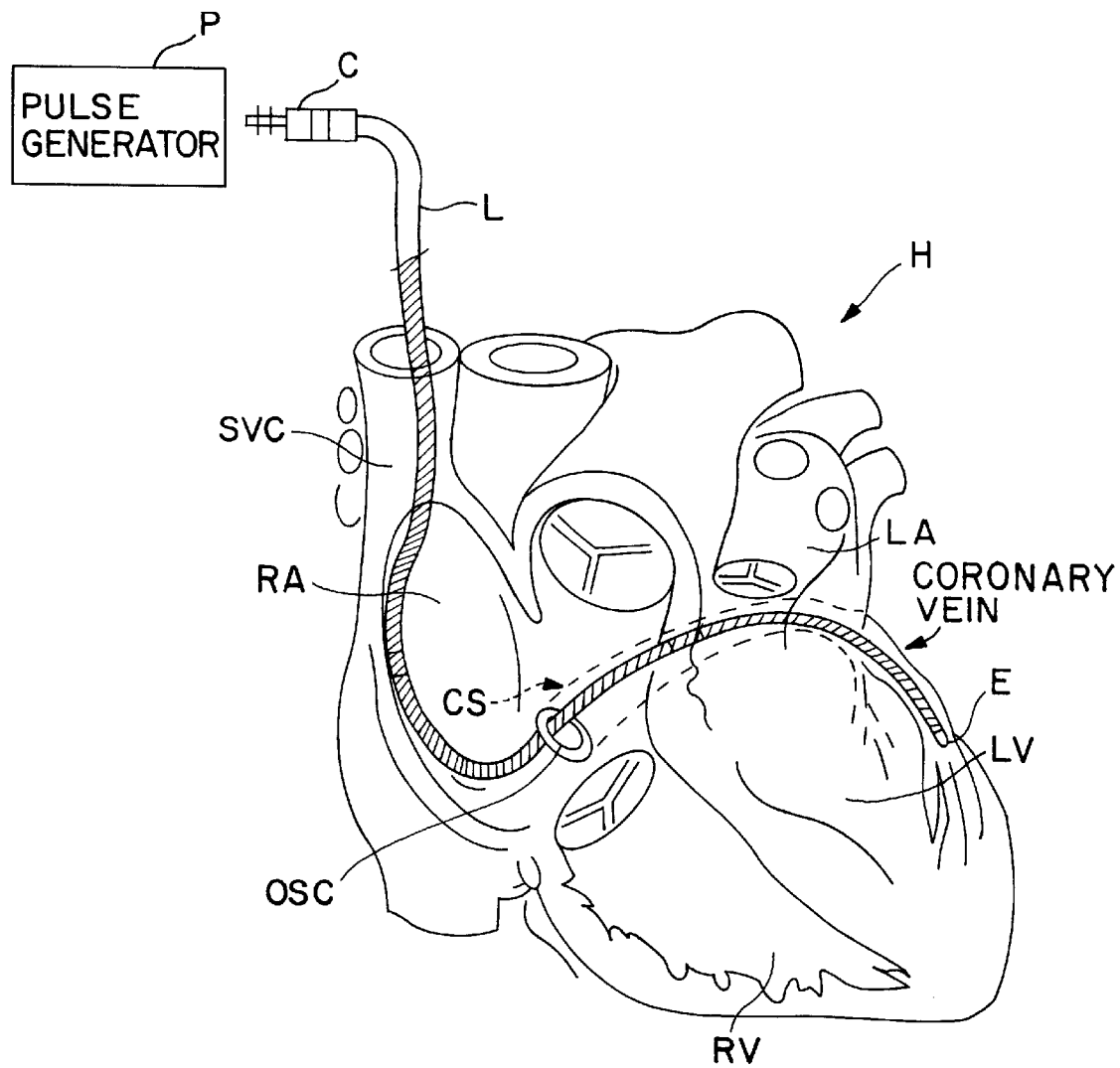
FIG. 1 is a partially cut-away view of a human heart in which a prior art pacing lead is implanted. The lead extends through the superior vena cava, right atrium, coronary sinus and a left coronary vein.

FIG. 1 shows a human heart H, partially cut away, in which an electrical pacing lead L is implanted. In accordance with the prior art, lead L has been placed endovascularly through the superior vena cava SVC and right atrium RA, and through the orifice of the coronary sinus OCS into the coronary sinus CS and into a left ventricular venous branch thereof. Pacing lead L includes at least one electrically insulated conductor extending lengthwise therethrough and at least one electrode E. Connector C at the proximal end of lead L is electrically connected via the insulated conductor to electrode E. A pulse generator P, usually implanted in a subcutaneous pocket in the chest wall of the patient, is connected to lead L via connector C. Because the left ventricular branches of the coronary sinus overly and are in physical proximity to the left ventricle LV, an electrical pulse can be delivered from pulse generator P via lead L and electrode E to stimulate contraction of the left ventricle. This lead arrangement is particularly suitable for pacing, cardioversion, or defibrillation of the left ventricle. Alternatively, with appropriate electrode placement, this lead arrangement can be used for sensing electrical activity in the vicinity of the left atrium or left ventricle, or for stimulating the left atrium. In combination with a second lead (not shown) disposed in the right ventricle RV, this lead arrangement can be used to effect bi-ventricular pacing for the treatment of congestive heart failure, as well as other medical conditions.

Placing a lead or other elongate medical device such as a catheter or cannula through the superior vena cava and right atrium into the orifice of the coronary sinus can be quite difficult, even with the use of fluoroscopy to monitor the location of the distal end of the medical device. The angles that the cannula must traverse are difficult to negotiate, even if the location of the orifice of the coronary sinus is generally known. In patients with distorted cardiac anatomy, such as that associated with congestive heart failure, the orifice of the coronary sinus can be more difficult to locate. An improved device and method for facilitating locating the coronary sinus is provided by the present invention, preferred embodiments of which are described below.

Figure 2:
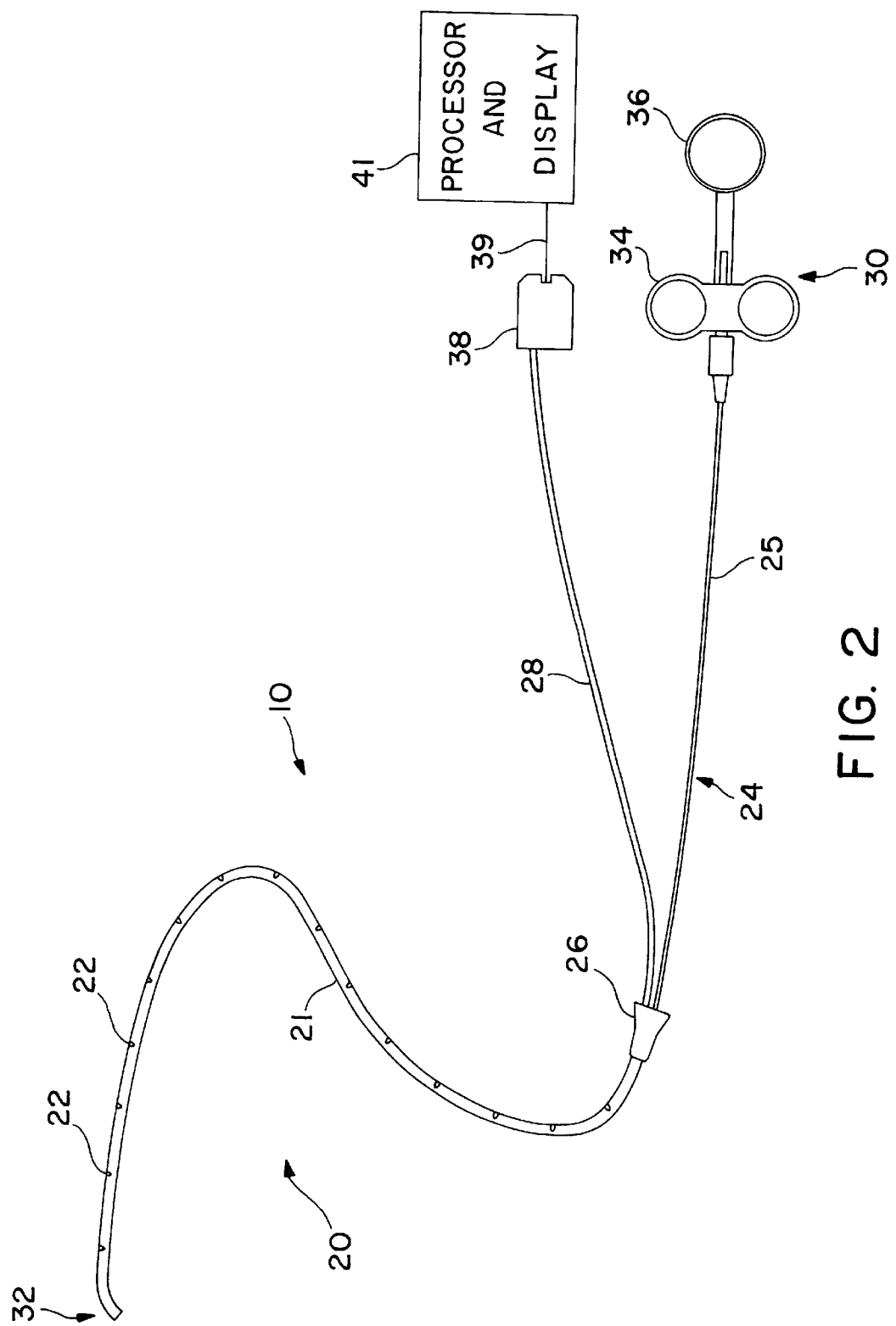
FIG. 2 is a plan view of an embodiment of a steerable, oximetric catheter of the present invention.

FIGS. 2, 3 and 4 show one embodiment of a steerable oximetric catheter 10 that can be used to practice the present invention. Catheter 10 includes a steerable cannula 20, including a blood-contacting sheath 21 that is fabricated from biocompatible polymers with low thrombogenicity. Radiopaque markers 22 may be placed along the length of the cannula 20 for fluoroscopic detection. Preferably encased within the sheath 21 of cannula 20 is a steering mechanism including a steerable guide 24, and a blood characteristic sensor such as a fiber optic oxygen sensor assembly 28. The steerable guide 24 and fiber optic oxygen sensor assembly 28 preferably run the entire length of cannula 20 to the distal end 32 and also extend from the proximal end 26 of cannula 20. The fiber optic oxygen sensor assembly 28 could be replaced by another sensor appropriate to other blood characteristics that are correlated with the blood of the coronary sinus, such as pH or $CO_2$ content.

Steerable guide 24 preferably includes an outer tube 25 and an internal wire 27 that runs from the distal end 32 to steering control module 30. Finger grips 34 and thumb grip 36 of control module 30 are reciprocably movable relative to each other along the axis of steerable guide 24. Thumb grip 36 is affixed to the outer tube 25 of guide 24 and finger grips 34 are affixed to the proximal end of the internal wire 27. The distal end of the internal wire 27 is affixed to the distal end of the outer tube 25 of steerable guide 24 in an axially offset manner as is known in the art. Alternatively, the outer tube 25 can be eliminated and the internal wire 27 instead affixed directly to the sheath 21 of cannula 20, in which case the thumb grip 36 could be affixed to sheath 21 with finger grips 34 being affixed to wire 27. By pulling finger grips 34 toward thumb grip 36, the internal wire 27 is placed in tension, thereby deflecting the distal end of steering guide 24, and hence sheath 21 and cannula 20, to one side. Through a combination of deflecting the distal end of cannula 20 via grips 34 and 36, and rotating the entire catheter 10 about its longitudinal axis, likewise via grips 34 and 36, the distal end of catheter 10 can be steered anywhere within a 360 degree range. Other steering mechanisms as known in the art can also be used.

The preferred blood characteristic sensor uses fiber optics to sense oxygen content, but alternatively, pH or $CO_2$ sensors can be used. The preferred fiber optic assembly 28 includes a pair of optical fibers 29 and 31 encased in a tube 33. These fibers run the entire length of assembly 28 and are connected at their proximal end to a photodetector optical module 38. The distal ends of the optical fibers are exposed at the distal end of assembly 28, and hence at the distal end 32 of cannula 20. Alternatively, the tube 33 can be eliminated and the optical fibers 29 and 31 can be carried inside sheath 21, or the steering guide 25, or on the outside of the cannula 20. Optical module 38 includes a light source in optical communication with the proximal end of one of the optical fibers 29,31, and a photodetector in optical communication with the proximal end of the other of the optical fibers 29,31. Light from the light source travels the length of the one optical fiber and exits at the distal end thereof, thereby illuminating the blood in the vicinity of the distal end 32 of the catheter 10. Light is reflected from the blood into the exposed distal end of the other optical fiber and is carried the length of that optical fiber to the photodetector in optical module 38.

According to a well known phenomenon, the color of the blood is a function of the percentage of oxygen saturation of the blood. Consequently, the color of the light absorbed by the blood, and hence the color of the light reflected back to the optical module 38, is also a function of oxygen content of the blood. The photodetector in optical module 38 is differentially responsive to different wavelengths of light, and generates an electrical signal indicative of the wavelength of the reflected light received via the optical fiber. The generated signal can be conveyed via suitable conductors 39 to a processor and display module 41 that can process the signal and display the percentage oxygen saturation in a form that is directly readable by a human, such as a digital display. Alternatively, the signal could be conveyed to a computing device for further manipulation prior to being displayed in human-readable form. One example of such a system is Optical Oximeter Apparatus and Method, U.S. Pat. No. 3,847,483, incorporated by reference.

Steerable oximetric catheter 10, which combines an oxygen sensing optical fiber assembly 28 with a wire-steerable guide 24 in a common cannula 20, is useful for locating the coronary sinus in accordance with the method of the present invention. The oxygen content of blood in the coronary sinus is known to be among the lowest in the human body. This phenomenon is exploited by the steerable oximetric catheter 10 to facilitate locating the coronary sinus. By monitoring the oxygen content or other characteristic of the blood in the vicinity of the distal end of catheter 10 in real time as catheter 10 is advanced through the right atrium, the operator can know whether the distal end of the catheter is either on or deviating from a path approaching the coronary sinus. If the sensed percentage of oxygen saturation continues to drop as catheter 10 is advanced, then the operator knows that the distal end of the catheter is getting closer to the coronary sinus. If the oxygen saturation begins to rise as the catheter is advanced, then the operator knows that the catheter is off course and he can correct the course using the steerability feature of the catheter. In effect, the operator is seeking to detect the low oxygen blood that exits from the coronary sinus into the right atrium. With an iterative procedure, the operator can make use of the percentage oxygen saturation being sensed in real time to guide and adjust his steering of the catheter to find the coronary sinus.

Figure 5:
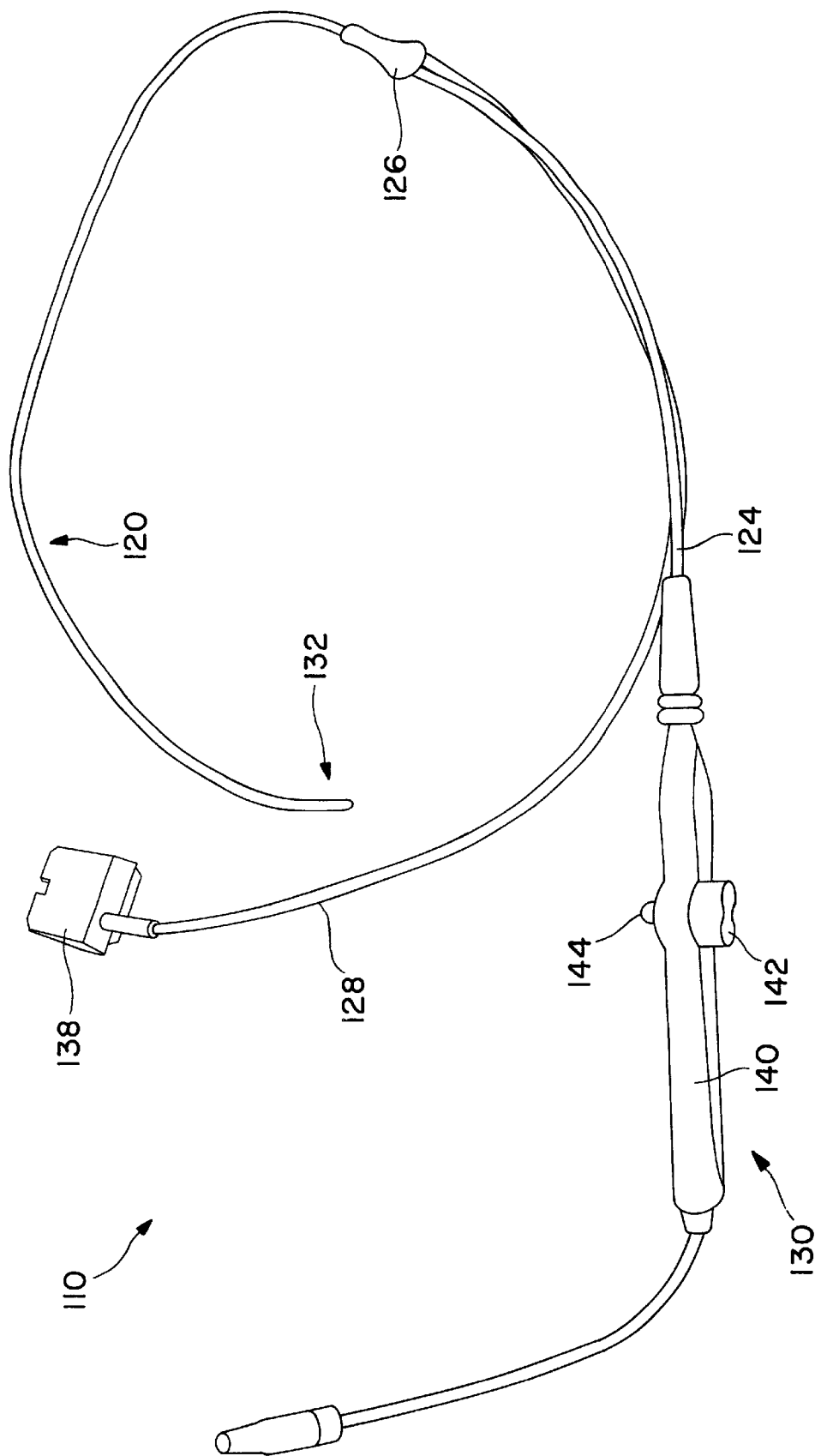
FIG. 5 is a plan view of another embodiment of a steerable, oximetric catheter of the present invention.
Figure 6:
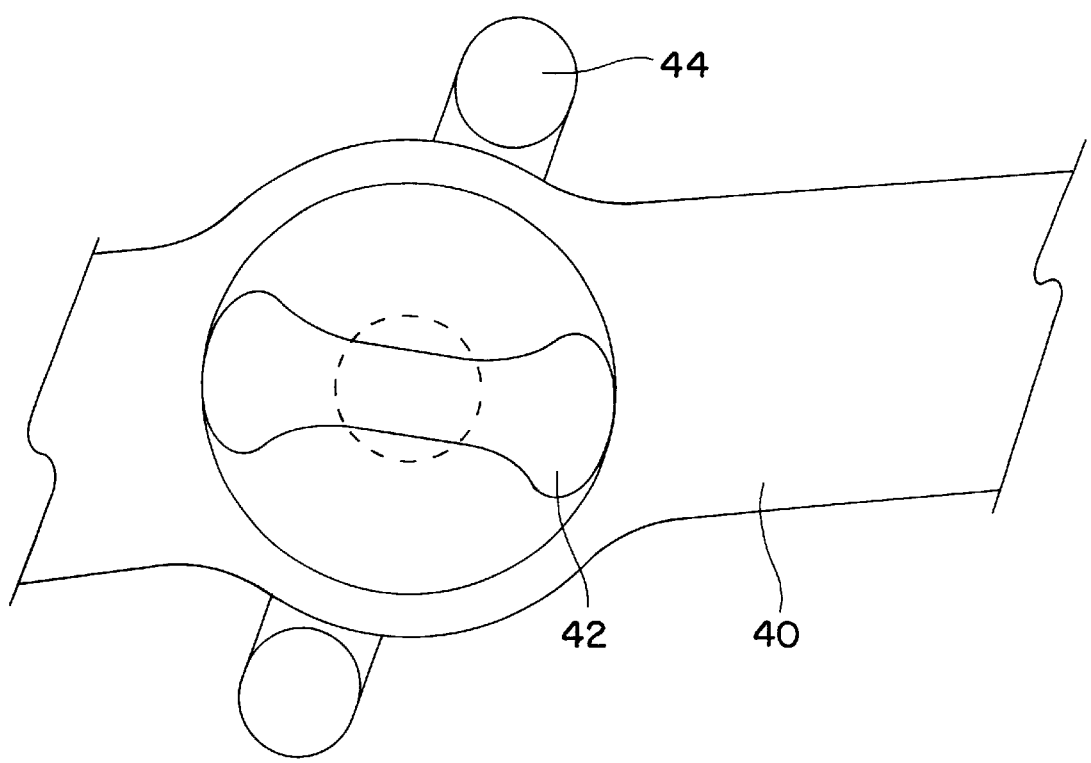
FIG. 6 is an enlarged plan view of a portion of the embodiment of FIG. 5.

FIGS. 5 and 6 show an alternative embodiment of a steerable oximetric catheter 110 that is substantially similar to the embodiment of FIGS. 2, 3 and 4, except that the steering control module 130 is somewhat different. Components that correspond in structure and function to the components described above with respect to the embodiment of FIG. 1 are indicated by similar reference numbers in the 100 series having the last two digits in common. The description above may be referred to for an understanding of the corresponding components of the embodiment of FIGS. 5 and 6. Steering control module 130, rather than having members that reciprocate axially relative to one another, has grip members that rotate relative to one another. Grip portion 140, which loosely corresponds to finger grip portion 34, is held in the operator's hand, while steering member 142 is gripped and rotated relative to grip portion 140. Steering member 142 is connected to the internal steering wire, whereas grip portion 140 is connected to the outer cannula of the steering guide 124. Rotation of member 142 relative to portion 140 places the steering wire in tension, effecting deflection of the distal end 132 of cannula 120. A locking lever 144 locks the steering member 142 in a selected position to maintain a selected deflection of the distal end 132 of cannula 120. Steering control module 130 is shown enlarged in FIG. 6 for clarity.

Figure 7:
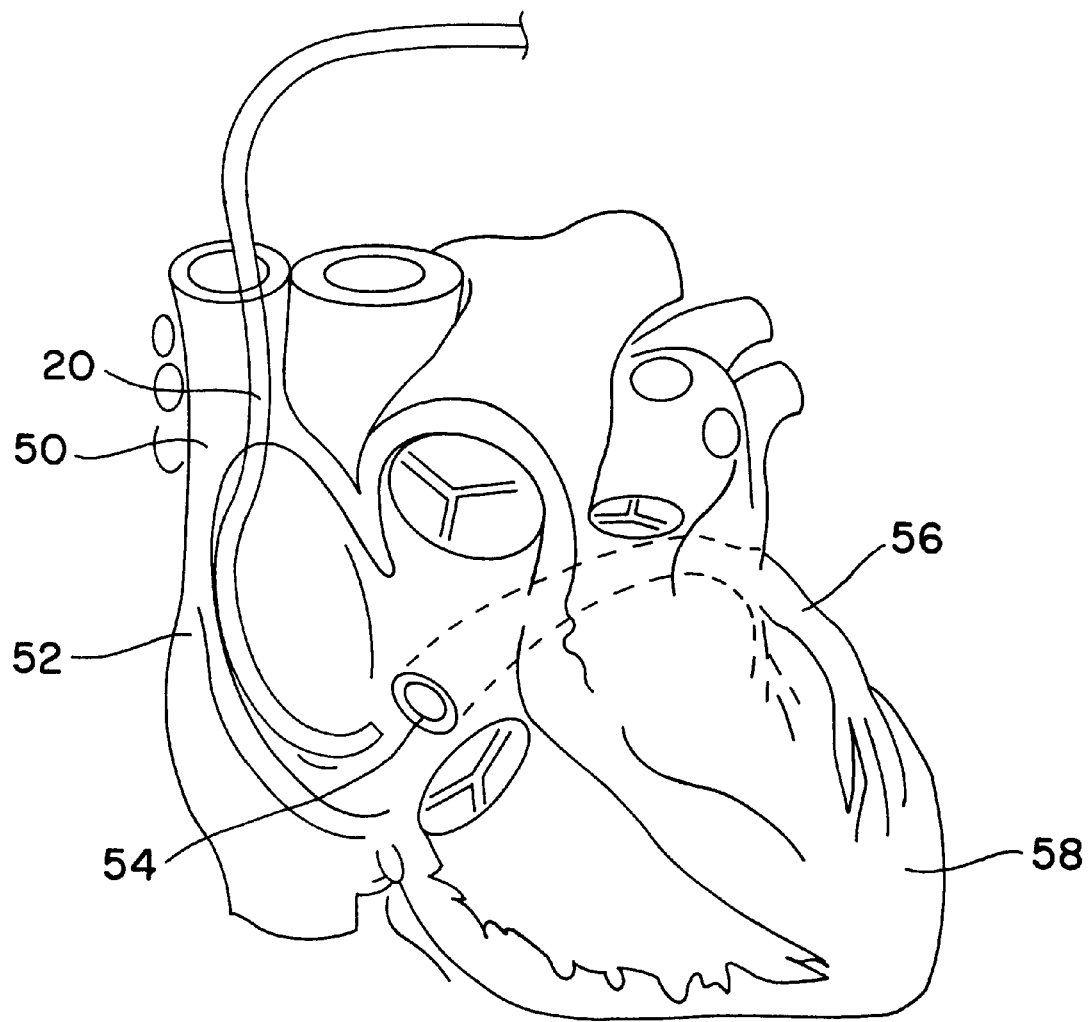
FIG. 7 is a cut-away view of a human heart, showing placement of the steerable oximetric catheters of FIGS. 2–6.

With the above description of preferred embodiments of steerable oximetric catheters in mind, the preferred procedures for practicing the inventive method for locating the coronary sinus will be described with reference to FIG. 7. In brief summary, a hollow, flexible, peel-away sheath 43 can be placed over the cannula 20 of catheter 10, for example, and slid to a position near proximal end 26. Cannula 20, with the peel-away sheath in place, can be introduced endovascularly under fluoroscopy through the superior vena cava 50 and into the right atrium 52. Using the steering mechanism in concert with the oximetry sensor of catheter 10, the coronary sinus 54 is located and the distal end of cannula 20 is steered into coronary sinus 54. Once the steerable catheter 10 is in the coronary sinus 54, the hollow, flexible peel-away sheath 43 can be slid distally over the cannula 20 toward distal end 32, guided into the coronary sinus 54, and held there. The steerable catheter 10 then can be withdrawn and removed, leaving the sheath 43 in place. Subsequently, a ventricular pacing lead can be advanced through the sheath 43 into the coronary sinus and placed into one of the coronary veins 56 associated with the left ventricle 58. The sheath 43 then can be withdrawn and peeled away from the lead.

Instead of using a sheath, the cannula 220 can be hollow defining a lumen 262 along its length as shown in cross section in FIG. 8. After the coronary sinus is located, the pacing lead is introduced through the lumen 262 and into one of the coronary veins 56. This system has the advantage of eliminating the use of the sheath, but does require that the cannula be large enough to carry the pacing lead.

Alternatively, the cannula 320 can be hollow defining a lumen 362 along its length, similarly to the cannula 220 of FIG. 8, but not including an embedded steering mechanism, as shown in FIG. 9. In use, a steering mechanism such as the steerable guide 24 of FIGS. 2, 3 and 4 could be inserted within the lumen 362 and used to steer the cannula 320. After the coronary sinus is located, the steering mechanism could be withdrawn from lumen 362, leaving lumen 362 open. The pacing lead could then be introduced through open lumen 362 and into the coronary sinus and great vein.

In yet another alternative arrangement, the cannula 420 can include a steering mechanism 427, optical fibers 429 and 431, and a pacing lead 464 embedded or otherwise disposed therein, as shown in FIG. 10. After the coronary sinus is located, the cannula 420 and lead 464 can be advanced as a unit into the coronary sinus and great vein. The proximal end of the cannula 420 can be cut off, or otherwise separated from the bulky steering controls and optical module. The pacing lead 464, including cannula 420, steering wire 427 and optical fibers 429 and 431 can be left permanently implanted as a unit.

In lieu of a sheath, a guidewire could be used to guide a hollow lead into the coronary sinus, with the lead riding over the guidewire instead of riding inside a sheath.

To place the steerable oximetric catheter 10 into the coronary sinus, the patient is placed upon a fluoroscopy table in a cardiac catheterization laboratory or in an operating room. Through a typical pacemaker incision below the clavicle, the subclavian vein or cephalic vein is accessed and cannulated with a hollow, flexible tube. The steerable, oximetric catheter 10 is placed through the hollow, flexible tube and into the superior vena cava, then advanced into the right atrium. The distal end of the oximetric assembly 28 is then connected to the optical module 38, which is connected to its associated processor and display 41. A right atrial baseline oxygen saturation is obtained.

Fluoroscopic evaluation of the end 32 of catheter 10 will permit the operator to estimate the approximate region in which the coronary sinus is located. The steerable, oximetric catheter 10 may then be advanced under fluoroscopy while percentage oxygen saturation is monitored. Any changes in oxygen saturation are noted. As the catheter 10 nears the coronary sinus orifice, the sensed oxygen saturation will drop. Using the steerable feature of the catheter, the site of the lowest oxygen saturation can be sought. The operator can continue to advance the steerable, oximetric catheter 10 under fluoroscopy and oximetric guidance into and through the coronary sinus orifice and into the coronary sinus. By monitoring the percentage oxygen saturation as the catheter is advanced, the operator may place the catheter 10 into the coronary sinus despite difficult angulations related to unusual physiology of the patient. Such difficulties could not be so easily overcome with fluoroscopic guidance alone.

The utility of the catheter and method of the present invention was demonstrated in an experiment involving an adult swine. A steerable, oximetric catheter was successfully placed into the coronary sinus of a pig. Conventional general endotracheal anesthesia was employed. The pig was placed in the decubitus position with the left side down. A right internal jugular cutdown was performed to access the central venous system. A prototype steerable oximetric catheter was created by attaching an Edwards central venous line with oximetry capability to a Blazer II model steerable catheter from EP Technologies. An in-vitro calibration of the oximetry probe was performed successfully. The prototype catheter was then introduced through the jugular vein into the superior vena cava and right atrium. Under fluoroscopy, the prototype catheter was placed into the coronary sinus using oximetric guidance. When the prototype catheter was placed in the coronary sinus, the percentage oxygen saturation dropped from the sixty percent range to the mid-thirty percent range. After verifying placement, the prototype was withdrawn into the right atrium. Again, under fluoroscopy, the prototype catheter was steered into the coronary sinus under oximetric guidance. Following successful coronary sinus cannulation, the prototype catheter was withdrawn and the pig euthenized.

Figure 11:
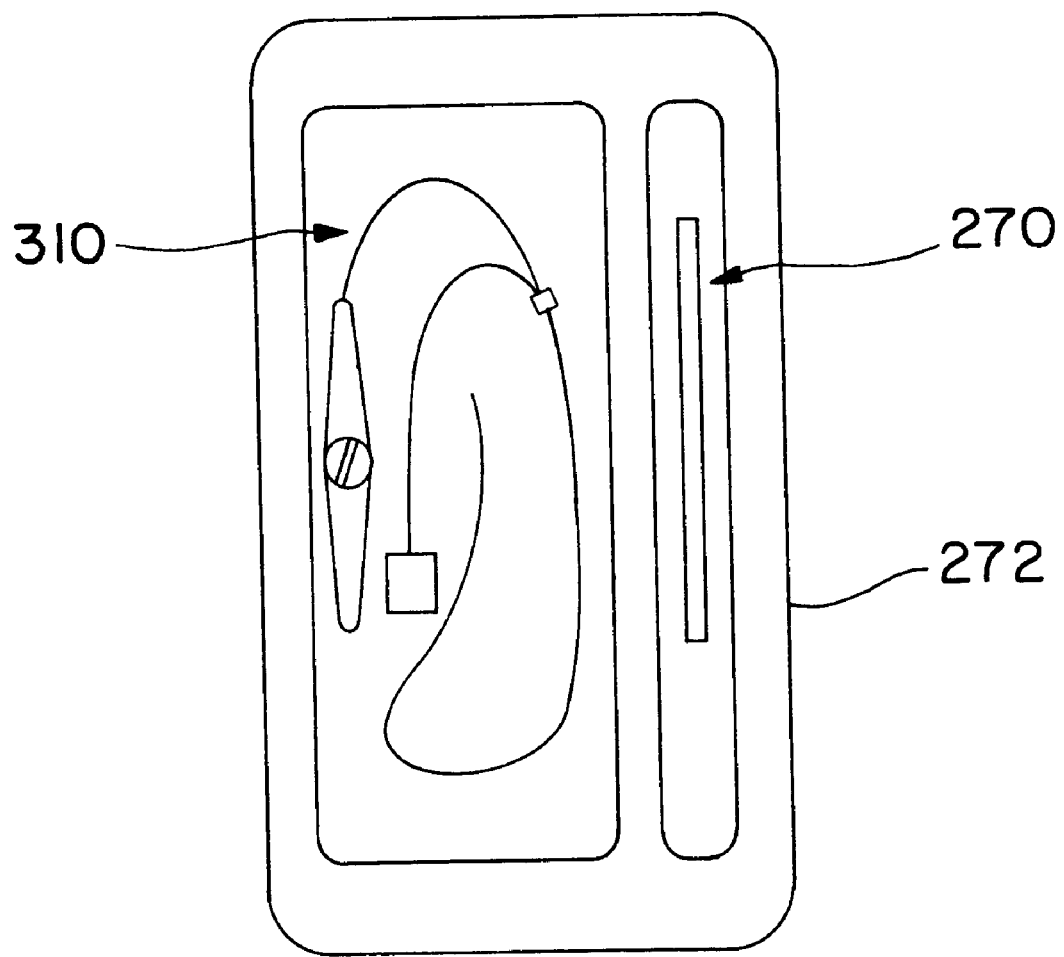
FIG. 11 is a plan view of a kit for performing the placement of an endovascular lead.

The present invention in one embodiment includes a kit for performing the placement of a pacing lead. As shown in FIG. 11, the kit includes a steerable oximetric catheter 310 and a sheath 270 in a sterile container 272. The kit can also include one or more of the following: catheter, sheath, syringe, large needle, dilator or a floppy wire, e.g., having a diameter of about 0.018 inches.

Although the present invention has been described in detail in terms of preferred embodiments, no limitation on the scope of the invention is intended.

What is claimed is:

1. A method of locating the coronary sinus of a heart, comprising the steps of:
    endovascularly introducing a catheter into a right atrium of the heart;
    sensing a characteristic of blood at the distal end of the catheter;
    qualitatively correlating the sensed characteristic of the blood at the distal end of the catheter with a characteristic of blood of the coronary sinus; and
    steering the catheter toward a region in which the sensed characteristic is qualitatively correlated with the blood of the coronary sinus.

2. The method of claim 1, wherein the catheter is oximetric and the step of sensing a characteristic comprises sensing percent oxygen saturation.

3. The method of claim 2, wherein the step of steering the catheter comprises qualitatively correlating the lowest percent oxygen saturation.

4. The method of claim 1, and further including the step of:

introducing the distal end of the catheter into the coronary sinus.

5. The method of claim 4, and further including the step of:

introducing a sheath over the catheter into the coronary sinus and withdrawing the catheter from the coronary sinus.

6. The method of claim 5, and further including the step of introducing a pacing lead through the sheath and into the coronary sinus.

7. The method of claim 6, and further including the step of introducing the pacing lead through the coronary sinus and into a vein associated with the left ventricle of the heart.

8. The method of claim 1 further including introducing a pacing electrode through a passageway in the catheter into the coronary sinus.

9. The method of claim 1, wherein the step of sensing a characteristic comprises sensing pH.

10. The method of claim 1, further comprising placing a pacing lead proximate to or through the coronary sinus of the heart, wherein placing a pacing lead comprises introducing the catheter into the right atrium of the heart and steering the catheter while concurrently monitoring at the distal end of the catheter the characteristic of blood indicative of blood in the coronary sinus to introduce the distal end of the catheter into the coronary sinus, and introducing a pacing lead into the coronary sinus.

11. The method of claim 10, wherein monitoring a characteristic of blood comprises sensing percent oxygen saturation.

12. The method of claim 10, wherein the step of sensing a characteristic of blood comprises sensing pH.

13. The method of claim 10, wherein the step of sensing a characteristic of blood comprises sensing percent $CO_2$ saturation.

14. The method of claim 10 wherein the pacing lead is fixed to the heart proximate to the coronary sinus.

15. The method of claim 10 wherein the catheter is introduced through the coronary sinus and into a great vein.

16. The method of claim 10 wherein the pacing lead is fixed in a great vein.

17. The method of claim 10 wherein the pacing lead is fixed in a coronary vein extending from a great vein.

18. The method of claim 10 further including advancing a hollow sheath over the catheter after the distal end of the catheter is introduced into the coronary sinus, removing the catheter and introducing the pacing lead through the hollow sheath.

19. The method of claim 1, wherein the catheter includes a hollow cannula and the pacing lead is introduced through the hollow cannula.

20. The method of claim 1, wherein the catheter includes a hollow cannula and a steering guide disposed therein, the steering guide being withdrawn from the hollow cannula and replaced by a pacing lead after the distal end of the catheter is introduced into the coronary sinus.

21. A method of locating the coronary sinus of the heart, comprising the steps of:

introducing a percent oxygen saturation sensor into a right atrium of the heart;

sensing the percent oxygen saturation with the oxygen saturation sensor; and steering the percent oxygen saturation sensor toward lowest percent oxygen saturation until the lowest percent oxygen saturation is located.

22. A method of locating the coronary sinus of a heart, comprising the steps of:

introducing a catheter having a distal end into a right atrium of the heart, the catheter further including a blood characteristic sensor for sensing the blood characteristic at the distal end;

sensing a characteristic of blood with the blood characteristic sensor; and steering the catheter to the coronary sinus based on the sensed characteristic of blood.

23. The method of claim 22, wherein the blood characteristic sensor is a percentage oxygen saturation sensor and the step of sensing a characteristic comprises sensing percent oxygen saturation.

24. The method of claim 23, wherein the oxygen saturation sensor comprises a optical fiber assembly.

25. The method of claim 22, wherein the blood characteristic sensor is a pH sensor and the step of sensing a characteristic comprises sensing blood acidity level.

26. The method of claim 22, wherein the blood characteristic sensor is a percentage $CO_2$ saturation sensor and the step of sensing a characteristic comprises sensing percent $CO_2$ saturation.

27. The method of claim 22 further including introducing a pacing electrode through a passageway in the catheter into the coronary sinus.

28. The method of claim 27, and further including the step of introducing a sheath over the catheter into the coronary sinus and withdrawing the catheter from the coronary sinus.

29. The method of claim 28, and further including the step of introducing the pacing lead through the coronary sinus and into a vein associated with a left ventricle of the heart.

30. The method of claim 22 including further introducing a pacing electrode through a passageway in the catheter into the coronary sinus.

* * * * *